(12) United States Patent
Yin

(10) Patent No.: US 12,065,441 B2
(45) Date of Patent: Aug. 20, 2024

(54) PYRAZOLOPYRIMIDINE DERIVATIVE, USE THEREOF AND PHARMACEUTICAL COMPOSITION

(71) Applicant: GENGLE THERAPEUTICS, INC., Kunshan (CN)

(72) Inventor: Jianming Yin, Hangzhou (CN)

(73) Assignee: GENGLE THERAPEUTICS, INC., Kunshan (CN)

( * ) Notice: Subject to any disclaimer, the term of this patent is extended or adjusted under 35 U.S.C. 154(b) by 763 days.

(21) Appl. No.: 16/972,605

(22) PCT Filed: Jun. 5, 2019

(86) PCT No.: PCT/CN2019/090095
§ 371 (c)(1),
(2) Date: Dec. 6, 2020

(87) PCT Pub. No.: WO2019/233434
PCT Pub. Date: Dec. 12, 2019

(65) Prior Publication Data
US 2021/0253576 A1     Aug. 19, 2021

(30) Foreign Application Priority Data

Jun. 6, 2018 (CN) .......................... 201810585715.6

(51) Int. Cl.
| | |
|---|---|
| *C07D 487/04* | (2006.01) |
| *A61P 1/00* | (2006.01) |
| *A61P 7/00* | (2006.01) |
| *A61P 17/00* | (2006.01) |
| *A61P 17/04* | (2006.01) |
| *A61P 19/02* | (2006.01) |
| *A61P 19/08* | (2006.01) |
| *A61P 29/00* | (2006.01) |
| *A61P 35/00* | (2006.01) |
| *A61P 37/00* | (2006.01) |
| *A61P 37/06* | (2006.01) |
| *C07D 471/04* | (2006.01) |

(52) U.S. Cl.
CPC .............. *C07D 487/04* (2013.01); *A61P 1/00* (2018.01); *A61P 7/00* (2018.01); *A61P 17/00* (2018.01); *A61P 17/04* (2018.01); *A61P 19/02* (2018.01); *A61P 19/08* (2018.01); *A61P 29/00* (2018.01); *A61P 35/00* (2018.01); *A61P 37/00* (2018.01); *A61P 37/06* (2018.01); *C07D 471/04* (2013.01)

(58) Field of Classification Search
CPC ....... C07D 487/04; C07D 471/04; A61P 1/00; A61P 7/00; A61P 19/02; A61P 29/00; A61P 35/00; A61P 37/00; A61P 17/06; A61P 19/08; A61P 37/06
USPC ......................................................... 544/262
See application file for complete search history.

(56) References Cited

FOREIGN PATENT DOCUMENTS

| | | |
|---|---|---|
| CN | 101448826 A | 6/2009 |
| CN | 102026999 A | 4/2011 |
| CN | 103797010 A | 5/2014 |
| CN | 103987713 A | 8/2014 |
| CN | 104024256 A | 9/2014 |
| WO | 2016173484 A1 | 11/2016 |

*Primary Examiner* — Taylor V Oh
(74) *Attorney, Agent, or Firm* — SOROKER AGMON NORDMAN PTE LTD

(57) ABSTRACT

Disclosed is a pyrazolopyrimidine derivative having a structure represented by general formula (I), a pharmaceutically acceptable salt, hydrate and metabolite formed by metabolism in any form thereof, and use in preparing drugs for preventing and/or treating indications associated with JAK kinase function, and a pharmaceutical composition prepared therefrom for preventing and/or treating indications associated with JAK kinase function. The present disclosure is a selective JAK kinase inhibitor, which has a pharmaceutical therapeutic effect on immunity and inflammatory responses by acting on JAK kinase.

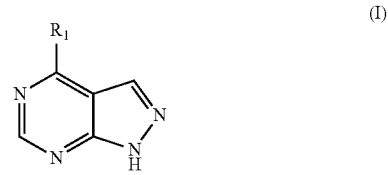

(I)

10 Claims, No Drawings

PYRAZOLOPYRIMIDINE DERIVATIVE, USE THEREOF AND PHARMACEUTICAL COMPOSITION

TECHNICAL FIELD OF THE INVENTION

The present disclosure relates to a pyrazolopyrimidine derivative, and use in preparing drugs for preventing and/or treating indications associated with JAK kinase function, and a pharmaceutical composition thereof.

BACKGROUND OF THE INVENTION

Cytokines affect differentiation, proliferation and activation of cells, and can regulate pro-inflammatory responses and anti-inflammatory responses. The signal transduction of varieties of cytokines includes the Janus kinase family (JAK) and signal transducers and activators of transcription (STAT) of protein tyrosine kinases. JAK kinases are intracellular non-receptor tyrosine kinases that can mediate cytokines and have a certain regulatory role in cell proliferation and function involved in immune responses. JAK kinase family has four members, namely, JAK kinase 1, JAK kinase 2, JAK kinase 3 and tyrosine kinase 2. In general, cytokines activate JAK kinases by binding to cytokine receptors, and activate STATs after JAK activation, and the activated STATs enter the nucleus to regulate gene expression. As the main signal transduction pathway mediated by cytokine receptors, the JAKs-STATs family may interact with other signal transduction pathways and participate in the development, differentiation, maturation, apoptosis and functional expression process of various immune and hematopoietic cells, and play an extremely important role in regulating the immune and inflammatory responses of the body.

The abnormal activation of JAKs-STATs pathway is closely related to many diseases. The activation of JAK/STAT in cancer can occur through reduction of cytokine stimulation and the like. Therefore, JAK kinase inhibitors can be used in the treatment of immune diseases such as ankylosing spondylitis, inflammatory diseases such as Crohn's disease, polycythemia vera, atopic dermatitis, psoriatic arthritis, essential thrombocytosis, myelofibrosis and cancers.

SUMMARY OF THE INVENTION

The technical problem to be solved by the present disclosure is to provide a novel pyrazolopyrimidine derivative, which is an ideal selective JAK kinase inhibitor.

The present disclosure also provides use of a pyrazolopyrimidine derivative, a pharmaceutically acceptable salt, hydrate and metabolite formed by metabolism in any form thereof in preparing drugs for preventing and/or treating indications associated with JAK kinase function.

The present disclosure also provides a pharmaceutical composition for preventing and/or treating indications associated with JAK kinase function.

To solve the above problem, one technical solution employed by the present disclosure is as follows.

A pyrazolopyrimidine derivative having a structure represented by general formula (I), a pharmaceutically acceptable salt, hydrate and metabolite formed by metabolism in any form thereof.

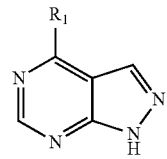

wherein:

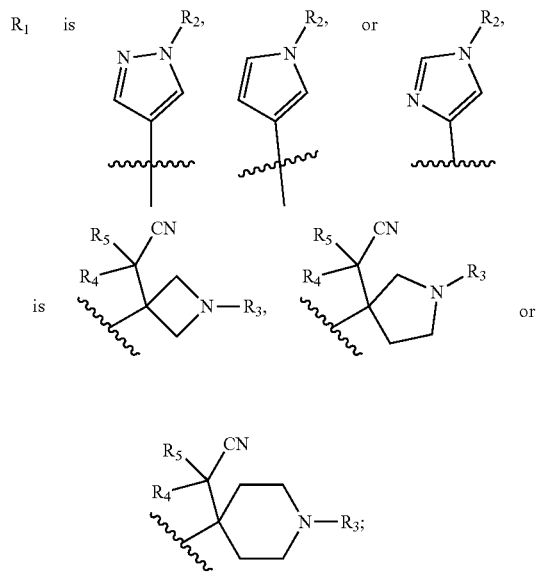

wherein, $R_3$ is

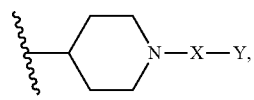

$SO_2R_6$ or $C(O)R_6$;

X is $C(=O)$, $C(=O)N(R_7)$, $C(=O)C(R_7)_2$, $S(=O)_2$, $C(=O)O$, $C(=O)OC(R_7)_2$ or $C(=O)N(R_7)C(R_7)_2$, $R_7$ is H or $C_{1-6}$ alkyl;

Y is $C_{1-6}$ alkyl, $C_{3-14}$ cycloalkyl, $C_{2-13}$ heterocyclic alkyl, $C_{6-14}$ aryl or $C_{3-14}$ heteroaryl which is unsubstituted or substituted by one or more selected from fluorine, chlorine, bromine, cyano, nitro, $C_{1-6}$ alkyl, $C_{2-6}$alkenyl, $C_{2-6}$ alkynyl and $C_{1-6}$ haloalkyl;

$R_6$ is selected from unsubstituted or halogenated hydrocarbyl, $NHCH_3$, $N(CH_3)_2$, phenyl, pyridyl, and pyrimidinyl;

$R_4$ and $R_5$ are independently selected from H, fluorine, chlorine and bromine;

non-exchangeable hydrogen in the pyrazolopyrimidine derivative having a structure represented by general formula (I), a pharmaceutically acceptable salt, hydrate and metabolite formed by metabolism in any form thereof, is unsubstituted, or partially or fully substituted by deuterium.

According to some preferred aspects of the present disclosure, $R_2$ is

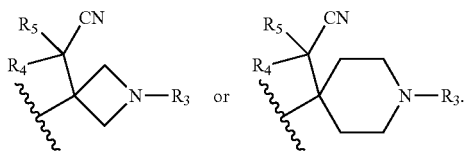

According to some preferred aspects of the present disclosure, X is $S(=O)_2$ or $C(=O)$.

According to some preferred aspects of the present disclosure, Y is methyl, ethyl, propyl, isopropyl, or butyl; or Y is 6-membered heteroaryl substituted by one or more of fluorine, chlorine, bromine, cyano, nitro, $C_{1-6}$ alkyl, $C_{2-6}$ alkenyl, $C_{2-6}$ alkynyl and $C_{1-6}$ haloalkyl. Wherein, $C_{1-6}$ alkyl may be methyl, ethyl, n-propyl, isopropyl, cyclopropyl, n-butyl, isobutyl, tert-butyl, etc.; $C_{2-6}$ alkenyl may be vinyl, propenyl, butenyl, pentenyl, hexenyl, etc.; $C_{2-6}$ alkynyl may be ethynyl, propynyl, 1-butynyl, 1-pentynyl, 2-pentynyl, 1-hexynyl, 2-hexynyl, etc.; $C_{1-6}$ haloalkyl may be methyl, ethyl, n-propyl, isopropyl, cyclopropyl, n-butyl, isobutyl, tert-butyl, etc. substituted by one or more selected from fluorine, chlorine and bromine; the 6-membered heteroaryl may be phenyl substituted by one or more selected from nitrogen atom, sulfur atom and oxygen atom.

According to some preferred aspects of the present disclosure, the 6-membered heteroaryl contains one nitrogen atom, and a carbon atom connected to the X on the 6-membered heteroaryl is in a meta- or para-position relative to the nitrogen atom on the 6-membered heteroaryl. Wherein, the 6-membered heteroaryl 3 may be phenyl substituted by one or more selected from nitrogen atom, sulfur atom and oxygen atom.

According to some preferred aspects of the present disclosure, $R_6$ is unsubstituted or halogenated straight-chain hydrocarbyl or cycloalkyl, or straight-chain hydrocarbyl or branched-chain hydrocarbyl containing at least one double bond, and the number of carbon atoms in $R_6$ is 1-20. Wherein, the straight-chain hydrocarbyl may includes straight-chain alkyl, straight-chain alkenyl, and straight-chain alkynyl, the straight-chain alkyl may be methyl, ethyl, n-propyl, n-butyl, n-pentyl, and n-hexyl. etc.; the straight-chain alkenyl may be vinyl, n-propenyl, n-butenyl, n-pentenyl, n-hexenyl, etc.; the straight-chain alkynyl may be ethynyl, n-propynyl, n-butynyl, n-pentynyl, n-hexynyl, etc.; the branched-chain hydrocarbyl may be isopropyl, isobutyl, isopentyl, neopentyl, etc.; the cycloalkyl may be cyclopropyl, cyclobutyl, cyclohexyl, etc..

According to some further preferred aspects of the present disclosure, $R_6$ is unsubstituted or halogenated $C_{1-6}$ alkyl. Wherein, $C_{1-6}$ alkyl may be methyl, ethyl, n-propyl, isopropyl, cyclopropyl, n-butyl, isobutyl, tert-butyl, etc..

According to some preferred and specific aspects of the present disclosure, $R_2$ is

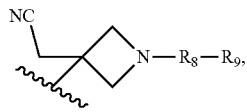

wherein, $R_8$ is absent, or is

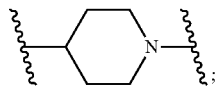

$R_9$ is

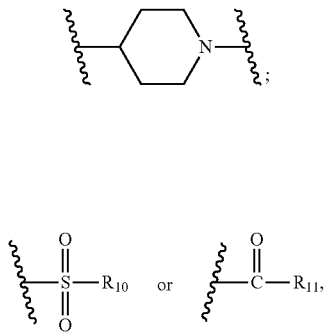

$R_{10}$ is methyl, ethyl, propyl, or isopropyl, $R_{11}$ is pyridyl substituted by at least one selected from fluorine, chlorine, bromine, and halogenated $C_{1-6}$ alkyl, and an atom connected to a carbon atom of carbonyl on the pyridyl is in a para-position relative to the nitrogen atom on the pyridyl. Wherein, $C_{1-6}$ alkyl may be methyl, ethyl, n-propyl, isopropyl, cyclopropyl, n-butyl, isobutyl, tert-butyl, etc..

According to a specific aspect of the present disclosure, $R_8$ is absent, $R_9$ is

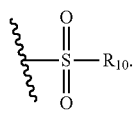

According to another specific aspect of the present disclosure, $R_8$ is

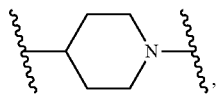

$R_9$ is

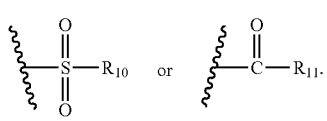

According to some preferred and specific aspects of the present disclosure, the pyrazolopyrimidine derivative, a pharmaceutically acceptable salt, hydrate and metabolite formed by metabolism in any form thereof, is one of compounds having structures represented by the following general formulas:

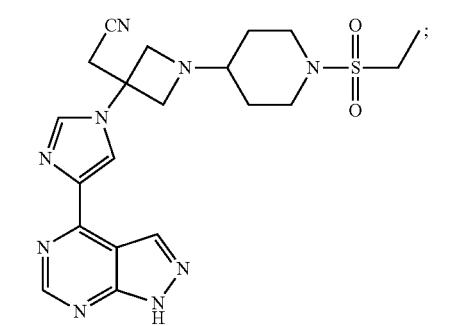
Ia
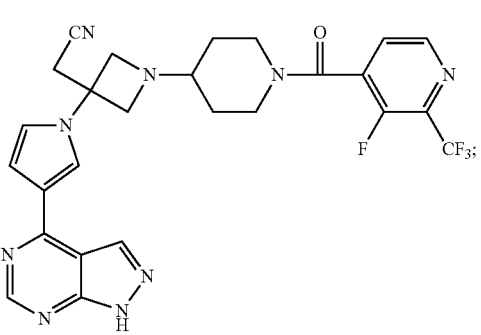
If
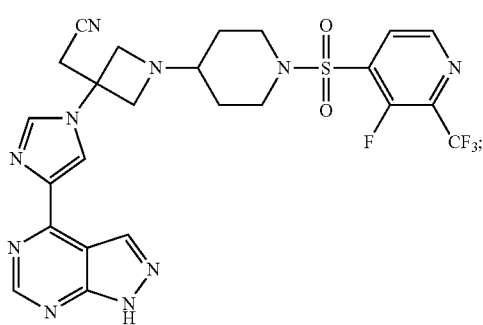
Ib
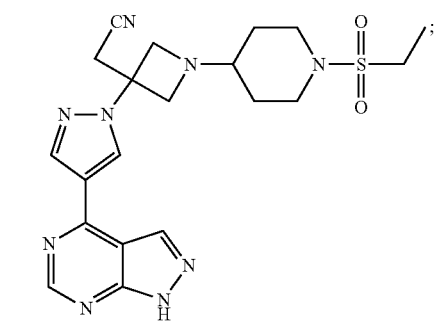
Ig
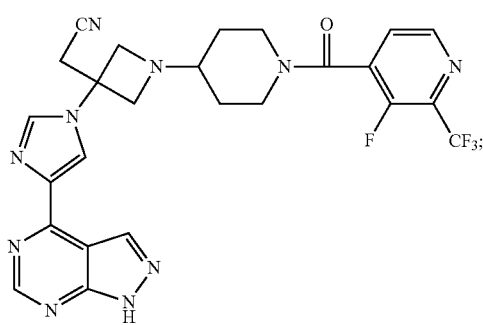
Ic
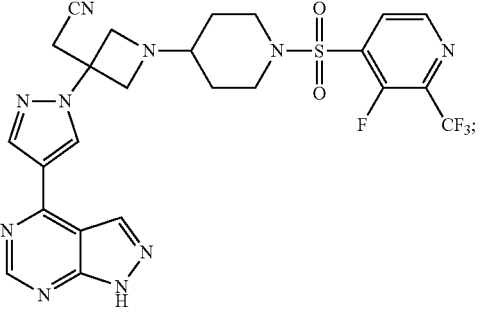
Ih
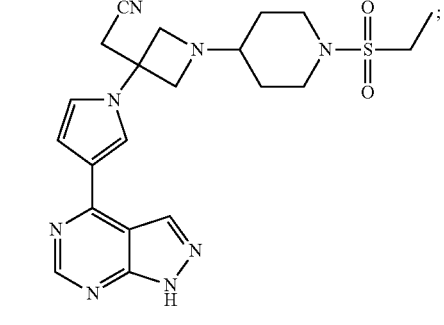
Id
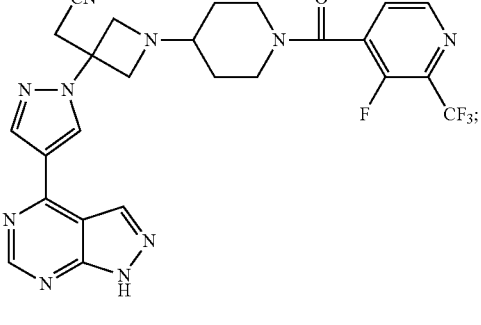
Ii
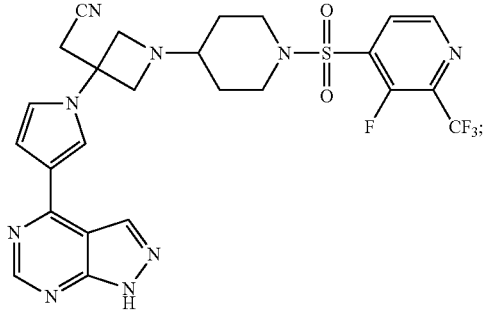
Ie
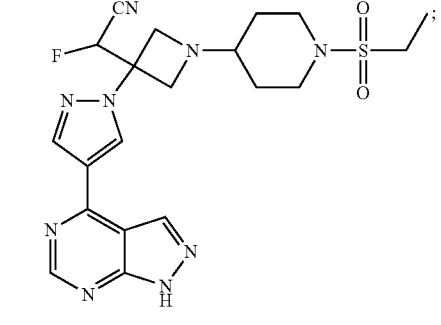
Ij

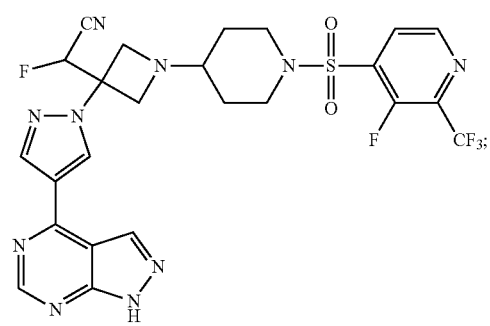
Ik
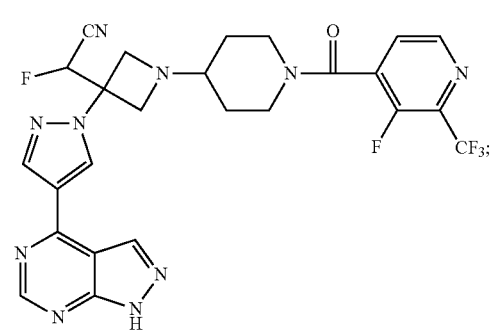
Il
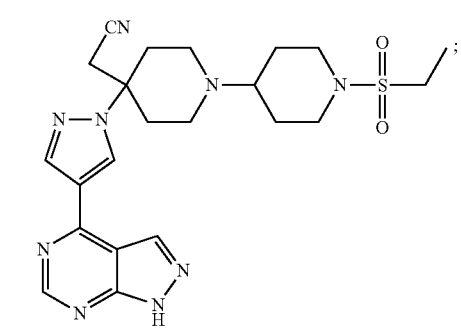
Im
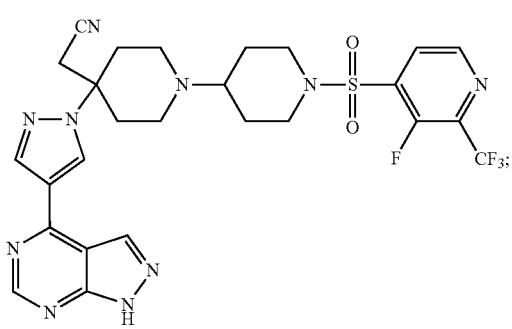
In
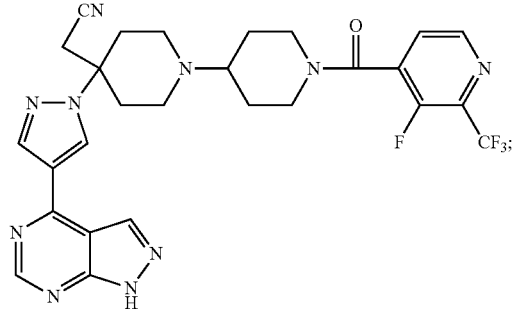
Io
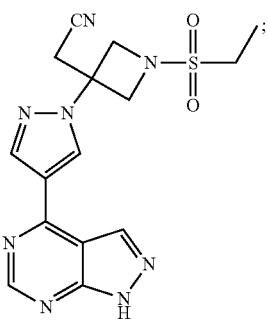
Ip
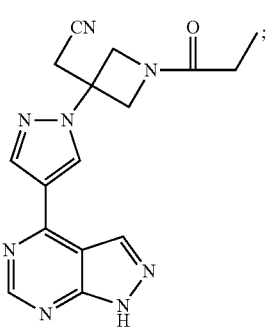
Iq
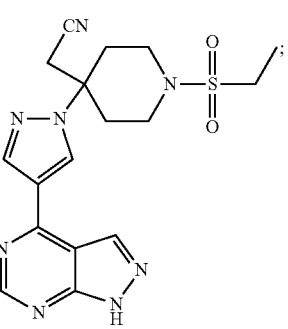
Ir
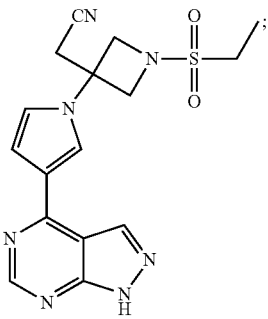
Is

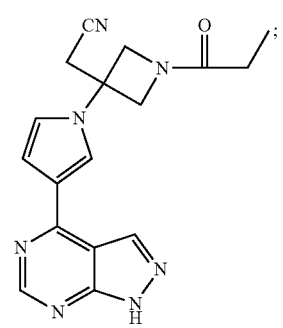 It;
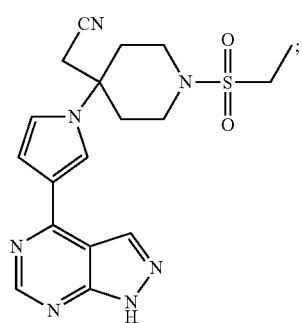 Iw;
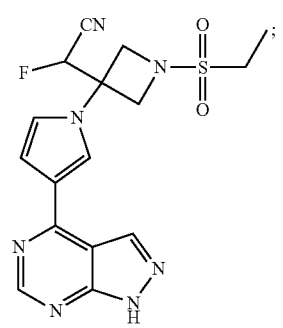 Ix;
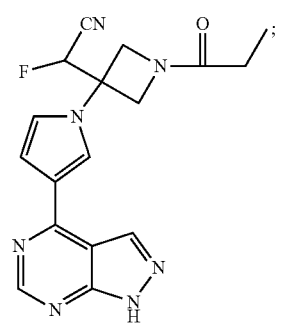 Iy;
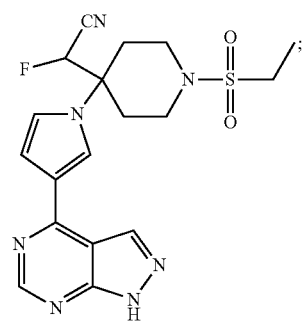 Iz;
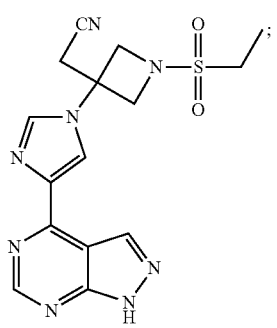 Iaa;
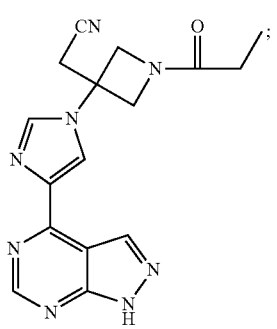 Iab;
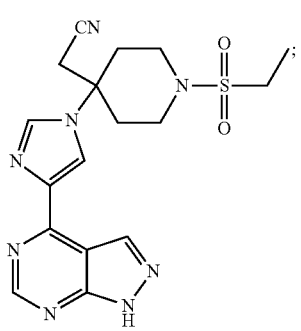 Iac;
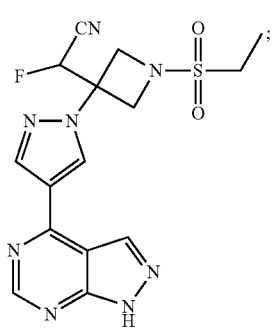 Iad;
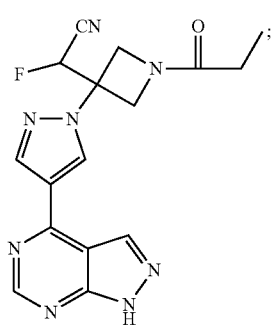 Iae;

Iaf

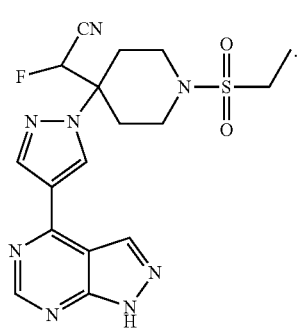

According to the present disclosure, the pyrazolopyrimidine derivative compound includes not only a single compound form, but also a mixture form of multiple compounds meeting the requirements of general formula (I), as well as different isomer forms of the same compound, such as racemates, enantiomers, diastereomers and the like. The pharmaceutically acceptable salt includes, but is not limited to, hydrochloride, phosphate, sulfate, acetate, maleate, methanesulfonate, benzenesulfonate, benzoate, toluenesulfonate, succinate, fumarate, fumarate, tartrate, gallate, citrate, etc.. The "prodrug of a compound of general formula (I)" refers to a substance that, when administered by a suitable method, can undergo metabolism or chemical reaction in the subject to transform into at least one compound of the structural formula (I) or its salt.

The pyridopyrimidine derivative of the present disclosure can be prepared by synthetic routes similar to those well-known in the chemical field, especially the compound of the present disclosure is synthesized according to the description contained herein. Reagents are generally obtained from commercial sources or easily prepared using methods well known to those skilled in the art.

Another technical solution provided by the present disclosure is: use of the pyrazolopyrimidine derivative having a structure of general formula (I), a pharmaceutically acceptable salt, hydrate and metabolite formed by metabolism in any form thereof in preparing drugs for preventing and/or treating indications associated with JAK kinase function.

According to some specific aspects of the present disclosure, the indications associated with JAK kinase function include immune diseases such as ankylosing spondylitis, inflammatory diseases such as Crohn's disease, polycythemia vera, atopic dermatitis, psoriatic arthritis, essential thrombocytosis, myelofibrosis and cancers.

Yet another technical solution provided by the present disclosure is: a pharmaceutical composition for preventing and/or treating indications associated with JAK kinase function, the pharmaceutical composition containing the pyrazolopyrimidine derivative having a structure of general formula (I), a pharmaceutically acceptable salt, hydrate and metabolite formed by metabolism in any form thereof.

Due to the implementation of the above technical solution, the present disclosure has the following advantages over the prior art:

The compound provided by the present disclosure is a novel pyrazolopyrimidine derivative, which is an ideal selective JAK kinase inhibitor, and has a certain pharmaceutical therapeutic effect on immunity and inflammatory responses by acting on JAK kinase.

DEFINITION OF TERMS

Unless otherwise defined, all technical and scientific terms used herein have the same meaning as commonly understood by one of ordinary skill in the art to which this disclosure belongs.

The term "isomer" refers to an isomer produced by the different arrangement of atoms in a molecule in space, and includes cis-trans isomers, enantiomers and conformational isomers. All stereoisomers are within the scope of the present disclosure. The compounds of the present disclosure may be a single stereoisomer or a mixture of other isomers such as a racemate, or a mixture of all other stereoisomers.

The term "salt" refers to a pharmaceutically acceptable salt formed by a compound of the present disclosure with an acid, the acid may be an organic or inorganic acid, specifically selected from phosphoric acid, sulfuric acid, hydrochloric acid, hydrobromic acid, citric acid, maleic acid, malonic acid, mandelic acid, succinic acid, fumaric acid, acetic acid, lactic acid, nitric acid, sulfonic acid, p-toluenesulfonic acid, malic acid, methanesulfonic acid or analogues thereof.

The term "solvate" refers to a form of a compound of the present disclosure that forms a solid or liquid complex by coordination with a solvent molecule. Hydrates are a special form of solvates in which coordination occurs with water. Within the scope of the present disclosure, the solvate is preferably a hydrate.

The term "crystal" refers to the various solid forms formed by the compounds described herein, including crystalline forms and amorphous forms.

The term "hydrocarbyl" refers to straight-chain, branched-chain or cyclic saturated or unsaturated substituent mainly consisting of carbon and hydrogen. It has preferably 1-20 carbon atoms, more preferably 1-12 carbon atoms. The term "alkyl" refers to a straight-chain, branched-chain or cyclic saturated hydrocarbyl group. The alkyl specifically includes methyl, ethyl, n-propyl, isopropyl, cyclopropyl, n-butyl, isobutyl, tert-butyl, cyclobutyl, n-pentyl, isopentyl, neopentyl, cyclohexyl, n-hexyl, isohexyl, 2,2,-dimethylbutyl and 2,3-dimethylbutyl, 16-alkyl, and 18-alkyl. The term "$C_{1-20}$ alkyl" refers to a straight-chain or branched-chain saturated hydrocarbyl group containing 1-20 carbon atoms. The substituted alkyl refers to alkyl substituted by a substituent. When an alkyl group is substituted, the substituent may substitute at any available point of attachment, and the substitution may be mono-substitution or poly-substitution. The substituent can be dependently selected from alkyl, alkenyl, alkynyl, alkoxy, alkylthio, alkylamino, deuterum, halogen, thiol, hydroxy, nitro, carboxy, ester, cyano, cycloalkyl, aryl, heteroaryl, cycloalkoxy, heterocycloalkoxy, cycloalkylthio, and oxo, and the substituent is usually placed before the alkyl group in naming.

The term "cycloalkyl" refers to saturated and/or partially unsaturated monocyclic or polycyclic cyclohydrocarbyl groups. A single ring generally includes 3-10 carbon atoms. Non-limiting examples of a monocyclic cycloalkyl group include cyclopropyl, cyclobutyl, cyclopentyl, cyclopentenyl, cyclohexyl, cyclohexenyl, cyclohexadienyl, cycloheptyl and the like. The polycyclic cycloalkyl group includes spiro cycloalkyl groups, fused cycloalkyl groups, and bridged cycloalkyl groups. The cycloalkyl group has or has no substituent. The substituent is independently selected from the group consisting of, but not limited to, alkyl, cycloalkyl, alkoxy, halogen, carboxy, ester, amino, amide, hydroxyl, cyano, nitro, aryl, heteroaryl.

The term "halogen" refers to fluorine, chlorine, bromine and iodine, preferably fluorine, chlorine and bromine.

The term "halogenated alkyl" refers to an alkyl group at least substituted by one halogen atom.

DETAILED DESCRIPTION OF EXEMPLARY EMBODIMENTS

In the following, the specific embodiments are combined to further explain the present disclosure in detail, however, the present disclosure is not limited to the following embodiments.

Embodiment 1

The current embodiment provides three specific pyrazolopyrimidine derivatives, namely, a compound of formula Ig, a compound of formula Ii, a compound of formula Ip.

The structural formulas of the compound of formula Ig, the compound of formula Ii, and the compound of formula Ip are respectively shown as follows:

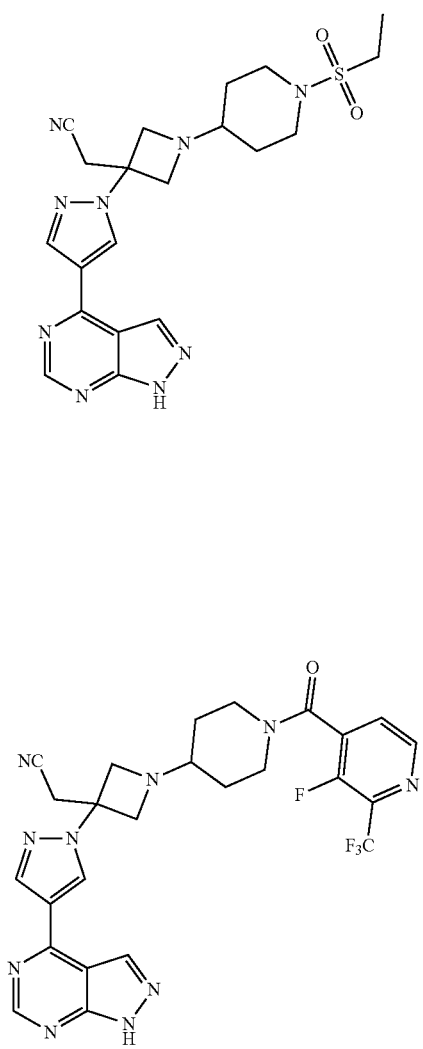

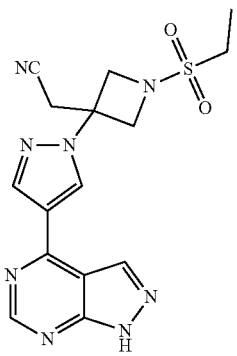

The three compounds can be obtained through the following synthesis route:

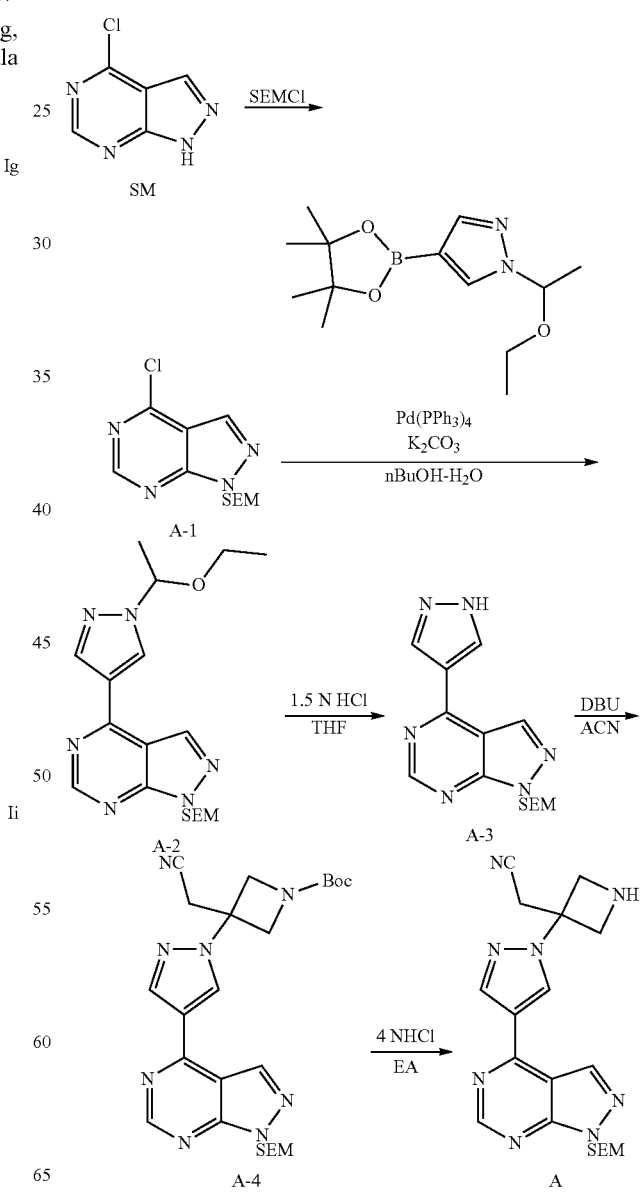

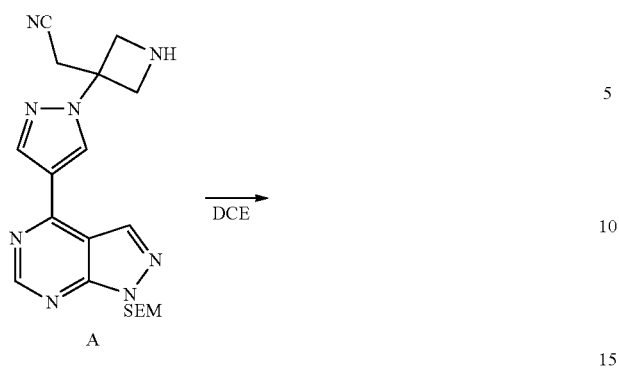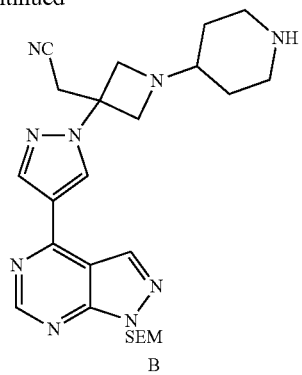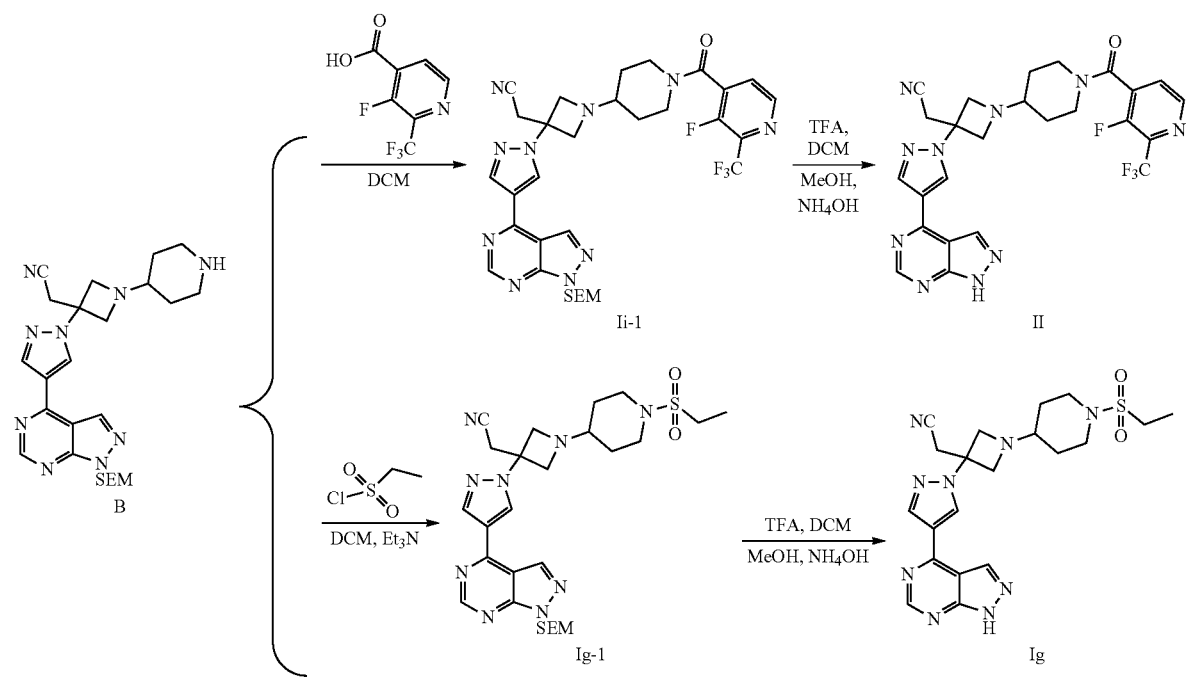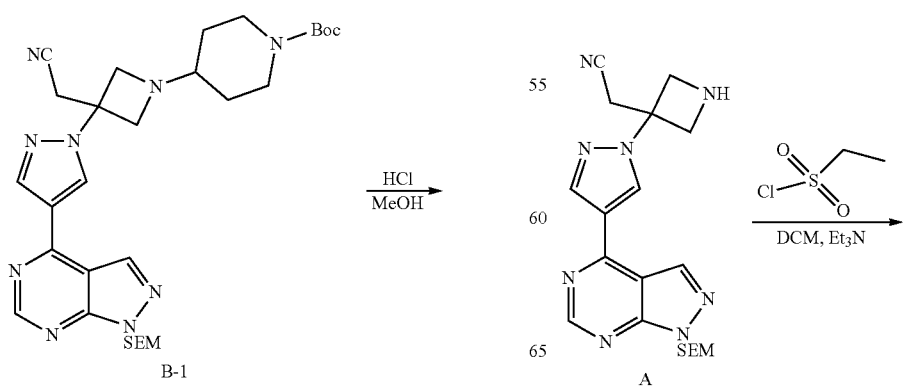

-continued

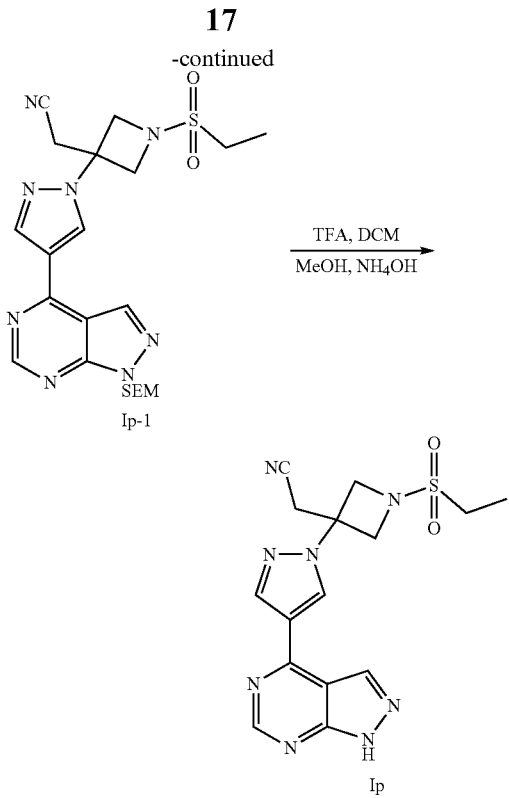

The process of the compounds specifically comprises the following steps:

1. Synthesis of Compound A-1:

At −20° C., a THF (50 mL) solution of DIPEA (63 g, 0.488 mol, N, N-Diisopropylethylaniine) was slowly added to a mixed solution of SM (50 g, 0.324 mol) and 2-(trimethylsilyl)ethoxymethyl chloride (62 g, 0.39 mol, SEMCl) in DMF (50 mL) and THF (200 mL), and the system was stirred at −20° C. for 3 hours, quenched by adding water, extracted with ethyl acetate, then the organic phase was dried, filtered, and concentrated to give a crude product, which was purified by flash column with petroleum ether and ethyl acetate (v/v=1/1) as eluant to give light yellow oil A-1 (45 g, 0.158 mol, yield: 32.6%).

2. Synthesis of Compound A-2:

Tetrakis(triphenylphosphine) palladium was added to a mixed solution of the compound A-1 (45 g, 0.158 mol), 1-(1-ethoxyethyl)-pyrazole-4-boronic acid pinacolate (63 g, 0.237 mol) and potassium carbonate (43.6 g, 0.316 mol) in n-butanol (200 mL) and water (200 mL), the system was replaced with argon four times, and the reaction solution was stirred overnight at 100° C., cooled to room temperature, filtered, extracted, dried, concentrated, and purified by flash column with petroleum ether and ethyl acetate (v/v=2/1) as eluant to give yellow oil A-2 (31 g, 0.1288 mol, yield: 81.5%).

3. Synthesis of Compound A-3:

A mixed solution of Compound A-2 (50 g, 0.1288 mol) in tetrahydrofuran (800 mL) and 1.5 N aqueous hydrochloric acid (100 mL) was stirred overnight at room temperature, concentrated, and then the concentrate was added to saturated sodium bicarbonate aqueous solution, stirred overnight, filtered, and the filter cake was dried to give white solid A-3 (31 g, 0.098 mol, yield: 76%).

4. Synthesis of Compound A-4:

A mixed solution of Compound A-3 (31 g, 0.098 mol), tert-butyl 3-(cyanomethylene)azetidine-1-carboxylate (29 g, 0.147 mol) and DBU (30 g, 0.196 mol) in acetonitrile (500 mL) was stirred at 70° C. for four hours, and then vacuum concentrated, and purified by flash column with petroleum ether and ethyl acetate (v/v=2/1) as eluant to give white solid A-4 (40 g, 0.0784 mol, yield: 80%).

5. Synthesis of Compound A:

A solution of Compound A-4 (31 g, 0.0784 mol) in ethyl acetate (800 mL, 4 N HCl) was stirred overnight at room temperature, concentrated, and then the concentrate was added to saturated sodium bicarbonate aqueous solution, stirred overnight, filtered, and the filter cake was dried to give white solid A, which was used directly in the next step without purification.

6. Synthesis of Compound B-1:

A solution of Compound A (from the previous step of reaction), N-tert-butoxycarbonyl-4-piperidone (23.4 g, 1.176 mol) and sodium triacetyl borohydride (42.3 g, 0.196 mol) in 1,2-dichloroethane (500 mL) was stirred overnight at room temperature, and then vacuum concentrated, and purified by flash column with petroleum ether and ethyl acetate (v/v=2/1) as eluant to give white solid B-1 (30 g, 0.05059 mol, yield: 83%).

7. Synthesis of Compound B:

A solution of Compound B-1 (30 g, 0.05059 mol) in methanol (600 mL, 4 N HCl) was stirred overnight at room temperature, concentrated, and then the concentrate was added to saturated sodium bicarbonate aqueous solution, stirred overnight, filtered, and the filter cake was dried to give white solid B (22 g, 0.04462 mmol, yield: 88%).

8. Synthesis of Compound Ii-1:

A solution of Compound B (16 g, 0.03245 mol), DIPEA (8.37 g, 0.0649 mmol), HATU (18.5 g, 0.048675 mmol, 0-(7-azabenzotriazol-1-yl)-N,N,N',N'-tetramethyluronium hexafluorophosphate) and 2-trifluoromethyl-3-fluoroisonicotinic acid (8.8 g, 0.042185 mmol) in dichloromethane (200 mL) was stirred overnight at to room temperature, then vacuum concentrated, and purified by silica gel column (ethyl acetate as a developing solvent) to give white solid Ii-1 (8 g, 0.01169 mol, yield: 36%).

9. Synthesis of Compound Ii:

A mixed solution of Compound Ii-1 (8 g, 0.01169 mol) in dichloromethane (50 mL) and trifluoroacetic acid (50 mL) was stirred at room temperature for one hour, then vacuum concentrated, and methanol (50 mL) and ammonia water (10 mL) were added to the system, and stirred at room temperature for two hours, the solvent was removed, the concentrate was added to water, extracted with dichloromethane, dried, concentrated, and purified by silica gel column to give white solid Ii (3.67 g, yield: 56.6%).

10. Synthesis of Compound Ig-1:

At 0° C., ethyl sulfonyl chloride was slowly and dropwise added to a solution of Compound B (14 g, 0.0284 mol) and Et$_3$N (5.7 g, 0.0568 mmol) in dichloromethane (200 mL), and the system was stirred at room temperature overnight, then vacuum concentrated, the concentrate was added to water, extracted with dichloromethane, dried, concentrated, and purified by silica gel column (ethyl acetate as a developing solvent) to give white solid Ig-1 (15 g, 0.02564 mol, yield: 90.3%).

11. Synthesis of Compound Ig:

A mixed solution of Compound Ig-1 (15 g, 0.02564 mol) in dichloromethane (100 mL) and trifluoroacetic acid (100 mL) was stirred at room temperature for one hour, then vacuum concentrated, and methanol (100 mL) and ammonia water (20 mL) were added to the system, and stirred at room temperature for two hours, the solvent was removed, the concentrate was added to water, extracted with dichloromethane, dried, and purified with dichloromethane/methanol=10/1 as a developing solvent to give white solid Ig (10.3 g, 0.022637 mol, yield: 88.3%).

12. Synthesis of Compound Ip-1:

At 0° C., ethyl sulfonyl chloride (7.5 g, 0.0585 mmol) was slowly and dropwise added to a solution of Compound A (16 g, 0.039 mol) and Et$_3$N (7.9 g, 0.078 mmol) in dichloromethane (200 mL), and the system was stirred at room temperature overnight, then vacuum concentrated, the concentrate was added to water, extracted with dichloromethane, dried, concentrated, and purified by silica gel column (ethyl acetate as a developing solvent) to give white solid Ip-1 (17 g, 0.03386 mol, yield: 86.8%).

13. Synthesis of Compound Ip:

A mixed solution of Compound Ip-1 (17 g, 0.03386 mol) in dichloromethane (100 mL) and trifluoroacetic acid (100 mL) was stirred at room temperature for one hour, then vacuum concentrated, and methanol (100 mL) and ammonia water (20 mL) were added to the system, and stirred at room temperature for two hours, the solvent was removed, the concentrate was added to water, extracted with dichloromethane, dried, concentrated, and purified by silica gel column (dichloromethane/methanol=10/1 as a developing solvent) to give white solid Ip (9.2 g, 0.02473 mol, yield: 73%).

Hydrogen nuclear magnetic resonance $^1$H-NMR and mass spectrometry were performed on the obtained target product Ii, and the results are as follows:

$^1$H-NMR (500 MHz) (DMSO-d6): δ ppm 14.09 (s, 1H), 8.99 (s, 1H), 8.87-8.85 (d, 2H), 8.68-8.66 (d, 1H), 8.55 (s, 1H), 7.91 (s, 1H), 4.10-4.07 (d, 1H), 3.78-3.86 (d, 2H), 3.61-3.57 (t, 4H), 3.46-3.42 (d, 1H), 3.30-3.27 (d, 1H), 3.08-3.04 (t, 1H), 2.51 (s, 1H), 1.77-1.64 (d, 2H), 1.31-1.23 (d, 2H); LCMS [M+H]+=555.2.

Hydrogen nuclear magnetic resonance $^1$H-NMR and mass spectrometry were performed on the obtained target product Ig, and the results are as follows:

$^1$H NMR (400 MHz, DMSO-d6) δ ppm 9.00 (s, 1H), 8.88 (d. J=9.2 Hz, 2H), 8.57 (s, 1H), 3.76 (d, J=8.0 Hz, 2H), 3.60-3.57 (m, 4H), 3.48-3.44 (m, 2H), 3.06-3.00 (m, 2H), 2.42 (m, 1H), 1.75-1.72 (m, 2H), 1.30-1.26 (m, 2H), 1.20 (t, J=7.6 Hz, 3H); LC-MS (ESI, m/z): 456 [M+1]+.

Hydrogen nuclear magnetic resonance $^1$H-NMR and mass spectrometry were performed on the obtained target product Ip, and the results are as follows:

$^1$H NMR (400 MHz, DMSO-d6) δ ppm 9.11 (s, 1H), 8.89 (d, J=9.2 Hz, 2H), 8.62 (s, 1H), 4.62 (d, J=9.6 Hz, 2H), 4.26 (d, J=9.2 Hz, 2H), 3.71 (s, 2H), 3.28-3.22 (q, 2H), 1.25 (t, J=7.6 Hz, 3H); LC-MS (ESI, m/): 373 [M+1]+.

Embodiment 2: Pharmacodynamic and Other Experiments

I. Compound Enzyme Activity Test:

1. Test Method:

The half-inhibition concentration IC$_{50}$ of the compound (the concentration of the compound required to inhibit the enzyme activity to 50%) is measured by mixing the fixed enzyme with a specific substrate and different concentrations of the test compound. The measurement method used was Caliper Mobility Shift Assay, the kinases measured were JAK1, JAK2, JAK3 and TYK2, and the standard reference compound used was staurosporine.

2. Test Result:

Table 1 summarizes the inhibition test results of compounds on enzyme activity. The results show that the target compounds (Ig, Ii, and Ip) have a strong inhibitory effect on kinases JAK1 and JAK2, and at the same time, the results show that the target compounds (Ig, Ii, and Ip) have weak inhibitory activity on JAK3 and TYK2, and have good selectivity. This selective inhibitory effect has important therapeutic significance for the treatment of diseases such as rheumatoid arthritis, polycythemia vera, psoriasis, essential thrombocytosis and myelofibrosis.

TABLE 1

Inhibition test results of compounds on enzyme activity

| Kinases | Kinase inhibitory activity (IC$_{50}$, nM) | | |
|---|---|---|---|
| | Compound Ig | Compound Ii | Compound Ip |
| JAK1 | 58 | 39 | 57 |
| JAK2 | 47 | 126 | 12 |
| JAK3 | 2063 | 3766 | 423 |
| TYK2 | 1231 | 2664 | 209 |

II. Pharmacokinetics Experiment

1. Test Method:

Experimental animals: mice, male and female, weight: 23-25 g;

Preparation of the test articles: The target compounds (Ig, Ii, and Ip) were prepared as 0.4 mg/mL (for intravenous administration) and 1.0 mg/mL (for oral administration), for later use. Administration route: oral administration/intravenous injection. Dosing volume and frequency: 5 mL/kg (intravenous injection) or 10 mL/kg (oral administration), single dose.

Sample collection: Blood was collected at the following time points, 5 min, 15 min, 30 min, 1 hr, 2 hr, 4 hr, 8 hr and 24 hr after administration.

2. Sample Analysis and Results

Sample analysis: LC-MS/MS method was used to detect the collected samples. The instrument model used was Triple Quad 6500+.

Pharmacokinetic data analysis: WinNolin was used to fit and calculate the obtained blood drug concentration data according to the non-compartmental model method, and partial results are summarized in Table 2.

TABLE 2

Pharmacokinetic parameters of the target compound calculated according to the non-compartmental model method

| Dosage (mg/kg) | Administration route | Pharmacokinetics experiment (unit) | Compound Ig | Compound Ii | Compound Ip |
|---|---|---|---|---|---|
| 2 | Intravenous injection N = 3M + 3F | CL (L/hr/kg) | 2.25 | 2.24 | 1.64 |
| | | Vss (L/kg) | 0.997 | 1.32 | 1.74 |
| | | Terminalt$_{1/2}$ (hr) | 0.390 | 0.834 | 1.39 |
| | | AUC$_{last}$ (ng*hr/mL) | 883 | 900 | 1203 |
| | | MRT$_{INF}$ (hr) | 0.446 | 0.596 | 1.06 |

TABLE 2-continued

Pharmacokinetic parameters of the target compound calculated according to the non-compartmental model method

| Dosage (mg/kg) | Administration route | Pharmacokinetics experiment (unit) | Compound Ig | Compound Ii | Compound Ip |
|---|---|---|---|---|---|
| 10 | Oral administration $N = 3M + 3F$ | $T_{max}$ (hr) | 0.375 | 1.00 | 0.250 |
| | | $C_{max}$ (ng/mL) | 1307 | 904 | 3383 |
| | | Terminal$t_{1/2}$ (hr) | 1.18 | 0.987 | 1.40 |
| | | $AUC_{last}$ (ng*hr/mL) | 2294 | 1706 | 5948 |
| | | F (%) | 51.7 | 37.9 | 99.4 |

The experimental results show that the compounds of the present disclosure have good pharmacokinetic characteristics.

The above embodiments are only representative. It can be seen from the above embodiments that the compounds of the present disclosure are ideal and highly effective JAK kinase inhibitors, which can be expected to be used for the treatment or prevention of diseases such as rheumatoid arthritis, polycythemia vera, psoriasis, essential thrombocytosis and myelofibrosis, and which can also be combined with different types of pharmaceutical salts to make into oral preparations (tablets or capsules, etc.). The tablets or capsules made with the compounds of the present disclosure can be taken one or more times a day. The compounds of the present disclosure can also be combined with other drugs to prepare compound preparations.

The embodiments described above are only for illustrating the technical concepts and features of the present disclosure, and are intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

What is claimed is:

1. A compound having a structure represented by formula (I), or a pharmaceutically acceptable salt thereof,

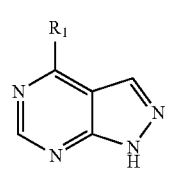
(I)

wherein:

R$_1$ is

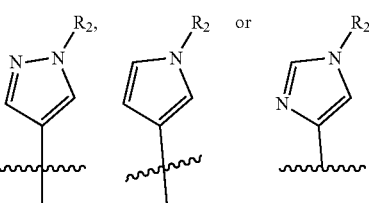

R$_2$ is

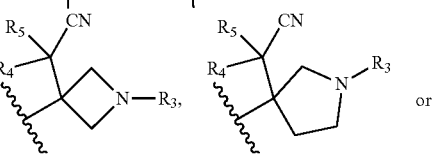

-continued

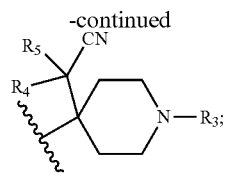

wherein, R$_3$ is

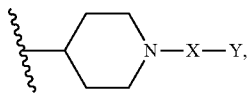

SO$_2$R$_6$ or C(O)R$_6$;
X is C(=O), C(=O)N(R$_7$), C(=O)C(R$_7$)$_2$, S(=O)$_2$, C(=O)O, C(=O)OC(R$_7$)$_2$ or C(=O)N(R$_7$)C(R$_7$)$_2$, R$_7$ is H or C$_{1-6}$ alkyl;
Y is C$_{1-6}$ alkyl, C$_{3-14}$ cycloalkyl, C$_{2-13}$ heterocyclic alkyl, C$_{6-14}$ aryl or C$_{4-14}$ heteroaryl which is unsubstituted or substituted by one or more selected from fluorine, chlorine, bromine, cyano, nitro, C$_{1-6}$ alkyl, C$_{2-6}$ alkenyl, C$_{2-6}$ alkynyl and C$_{1-6}$ haloalkyl;
R$_6$ is unsubstituted or halogenated hydrocarbyl, NHCH$_3$, N(CH$_3$)$_2$, phenyl, pyridyl, and pyrimidinyl;
R$_4$ and R$_5$ are independently selected from H, fluorine, chlorine and bromine:
non-exchangeable hydrogen in the compound having a structure represented by formula (I), or the pharmaceutically acceptable salt thereof, is unsubstituted, or partially or fully substituted by deuterium.

2. The compound or the pharmaceutically acceptable salt thereof according to claim 1, wherein R$_2$ is

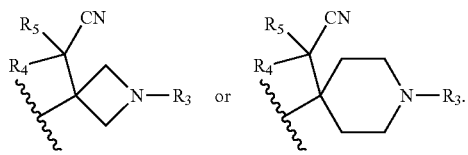

3. The compound or the pharmaceutically acceptable salt thereof according to claim 1, wherein X is S(=O)$_2$ or C(=O); and/or,
Y is methyl, ethyl, propyl, isopropyl, or butyl; or, Y is 6-membered heteroaryl substituted by one or more of fluorine, chlorine, bromine, cyano, nitro, C$_{1-6}$ alkyl, C$_{2-6}$ alkenyl, C$_{2-6}$ alkynyl and C$_{1-6}$ haloalkyl.

4. The compound or the pharmaceutically acceptable salt thereof according to claim 3, wherein the 6-membered heteroaryl contains one nitrogen atom, and a carbon atom connected to the X on the 6-membered heteroaryl is in a meta- or para-position relative to the nitrogen atom on the 6-membered heteroaryl.

5. The compound or the pharmaceutically acceptable salt thereof according to claim 1, wherein $R_6$ is unsubstituted or halogenated straight-chain hydrocarbyl or cycloalkyl, or straight-chain hydrocarbyl or branched-chain hydrocarbyl containing at least one double bond, and the number of carbon atoms in $R_6$ is 1-20.

6. The compound or the pharmaceutically acceptable salt thereof according to claim 5, wherein $R_6$ is unsubstituted or halogenated $C_{1-6}$ alkyl.

7. The compound or the pharmaceutically acceptable salt thereof according to claim 1, wherein $R_2$ is

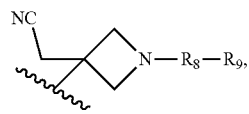

wherein $R_8$ is absent, or is

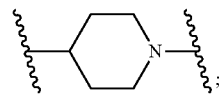 [SMILES: *C1CCN(*)CC1]

$R_9$ is

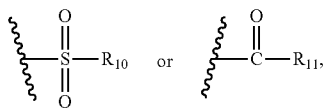

$R_{10}$ is methyl, ethyl, propyl, or isopropyl, $R_{11}$ is pyridyl substituted by at least one selected from fluorine, chlorine, bromine, and halogenated $C_{1-6}$ alkyl, and an atom connected to a carbon atom of carbonyl on the pyridyl is in a para-position relative to the nitrogen atom on the pyridyl.

8. The compound or the pharmaceutically acceptable salt thereof according to claim 1, wherein the compound, the pharmaceutically acceptable salt and, a hydrate thereof, is one of compounds having structures represented by the following formulas:

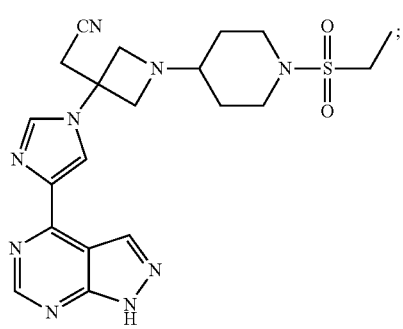

Ia

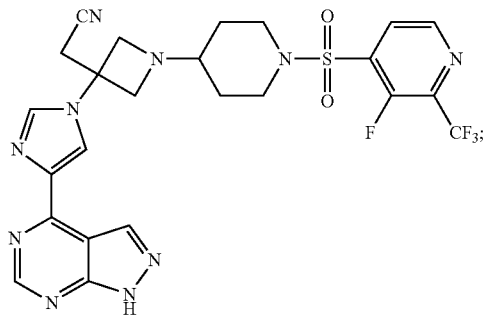

Ib

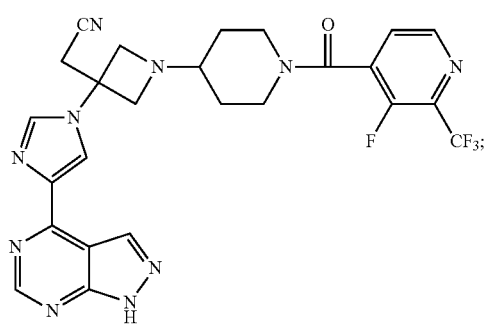

Ic

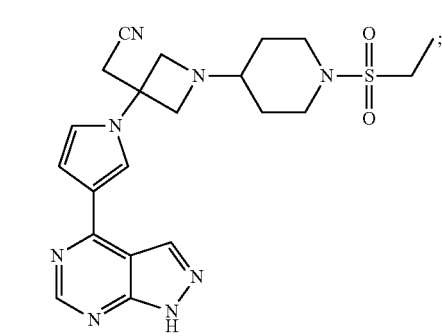

Id

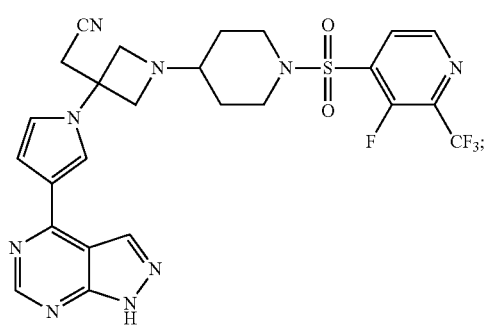

Ie

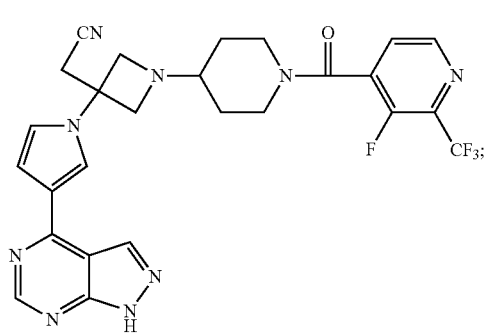

If

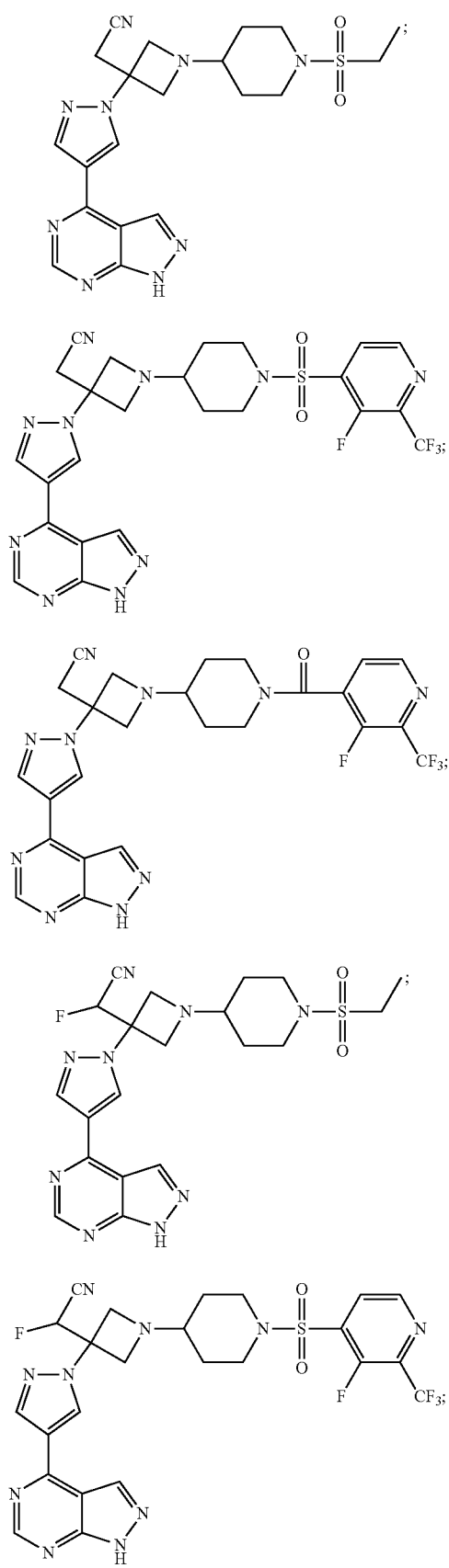
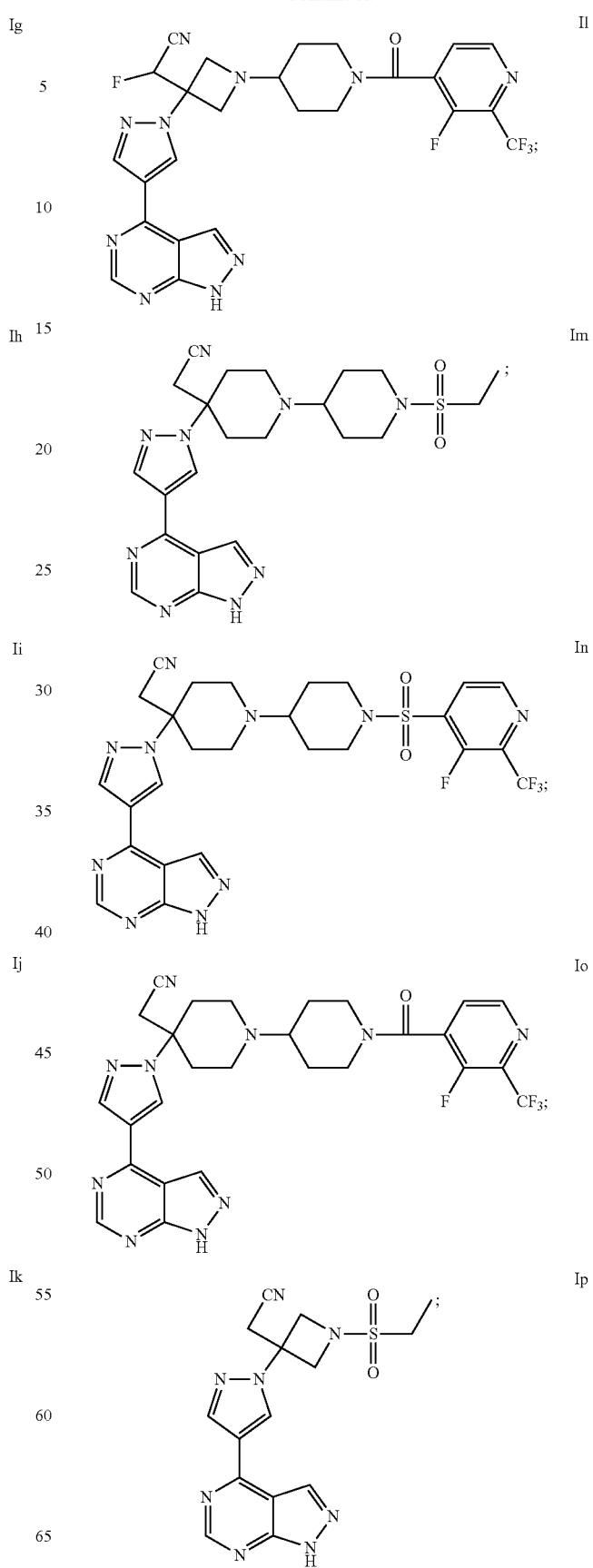

iq
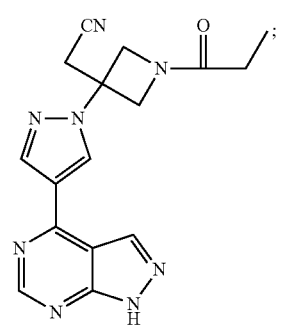
Ir
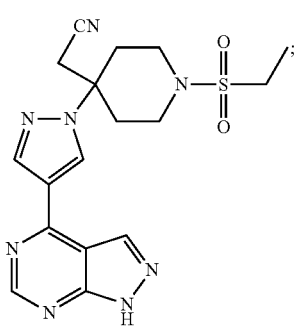
Is
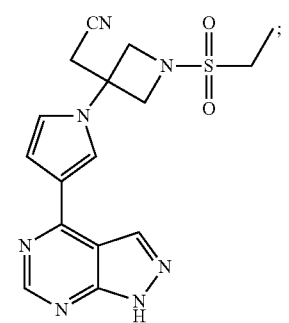
It
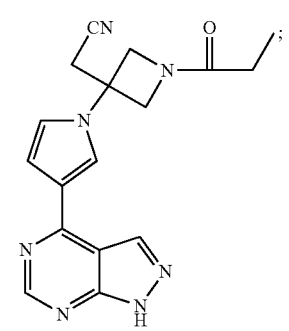
Iw
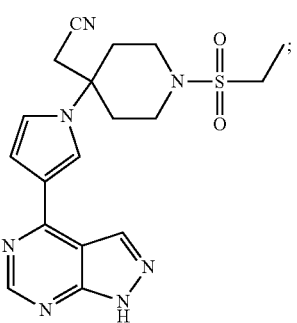
Ix
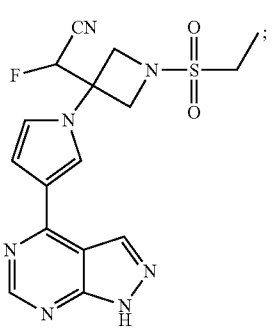
Iy
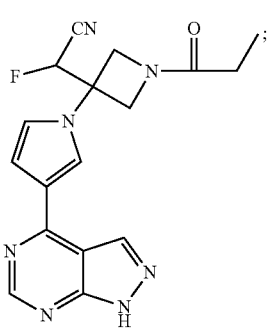
Iz
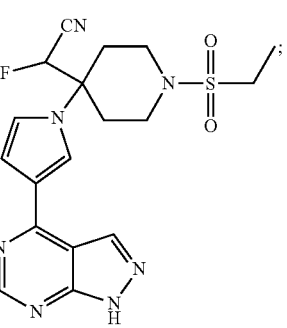
Iaa
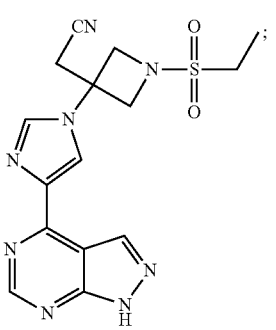
Iab
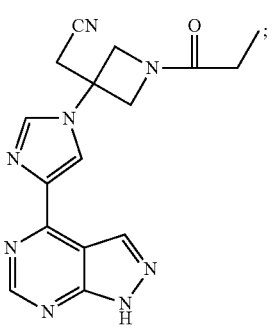

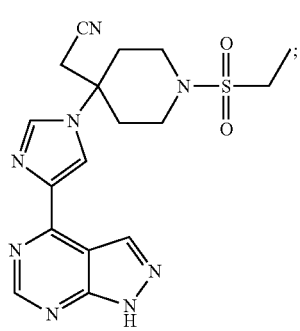
Iac

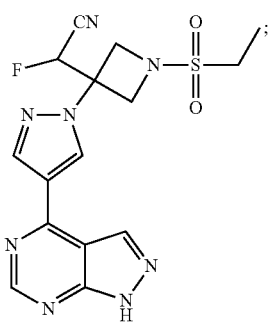
Iad

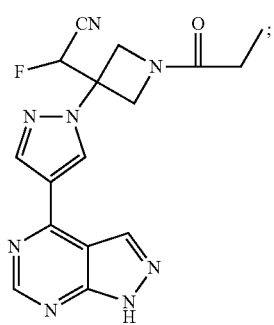
Iae

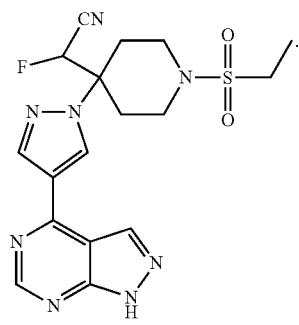
Iaf

9. A method for treating a disease or disorder, comprising administering an effective amount of the compound or the pharmaceutically acceptable salt thereof according to claim 1 to a subject in need thereof, wherein the disease or disorder is ankylosing spondylitis immune disease, Crohn's inflammatory disease, polycythemia vera, atopic dermatitis, psoriatic arthritis, essential thrombocytosis, or myelofibrosis.

10. A pharmaceutical composition comprising the compound or the pharmaceutically acceptable salt thereof according to claim 1.

* * * * *